United States Patent [19]
el Kouni et al.

[11] Patent Number: 5,670,331
[45] Date of Patent: Sep. 23, 1997

[54] METHODS FOR OPTIMIZING FLUOROPYRIMIDINE CANCER THERAPY

[75] Inventors: Mahmoud H. el Kouni; Fardos N. M. Naguib, both of Mt. Brook, Ala.

[73] Assignee: The University of Alabama Research Foundation, Birmingham, Ala.

[21] Appl. No.: 493,237

[22] Filed: Jun. 22, 1995

[51] Int. Cl.$^6$ .................................................. C12Q 1/48
[52] U.S. Cl. ............................................................ 435/15
[58] Field of Search .............................................. 435/15

[56] References Cited

PUBLICATIONS

Traut et al., Biochem. Pharm., 26, 2291–96 (1977).
Tampitag et al., Mol. Biochem. Parasitology, 18, 125–34 (1986).
Peters et al., Cancer Res., 46, 20–28, 1986.
Peters et al., Br. J. Cancer, 59, 327–34 (1989).

*Primary Examiner*—Johann Richter
*Assistant Examiner*—Laura R. Cross

[57] ABSTRACT

The present invention provides a method of predicting whether an individual will be intolerant to the effect of fluoropyrimidines comprising the step of measuring the activity of orotate phosphoribosyltransferase activity in a biological sample obtained from said individual. Also provided is a method of determining a non-toxic dose of 5-fluoruracil in an individual in need of fluoropyrimidine therapy, comprising the step of measuring the activity of 5-fluoruracil phosphoribosyltransferase (FUPRTase) in a biological sample obtained from said individual.

11 Claims, No Drawings

METHODS FOR OPTIMIZING FLUOROPYRIMIDINE CANCER THERAPY

BACKGROUND OF THE INVENTION

1. Field of the Invention

The present invention relates generally to the fields of biochemical pharmacology and cancer chemotherapy. More specifically, the present invention relates to an effective diagnostic test predictive of tolerance or intolerance in cancer patients scheduled for treatment with fluoropyrimidine cancer chemotherapeutic agents.

2. Description of the Related Art

For almost four decades, 5-fluorouracil (FUra) and its nucleosides (e.g., 5-fluoro-2'-deoxyuridine or FdUrd) despite their known clinical toxicities and extensive research to develop better, alternative drugs, have remained among the few "standard" drugs effective against solid tumors in man. 5-fluorouracil is used mainly for the treatment of colorectal, ovarian, renal, breast, and head and neck cancers. 5-fluoro-2'-deoxyuridine is used for the treatment of solid tumors, including hepatic metastases of advanced gastrointestinal adenocarcinomas, renal cell carcinomas, advanced ovarian cancer, and squamous cell carcinomas of the head and neck. These drugs are unique in that they are the only drugs in the market that show synergism in combination therapy with most other anticancer agents (e.g., radiotherapy or the antifolate methotrexate, etc.). Nevertheless, the clinical utility of the fluoropyrimidines is limited by the host-toxicity induced by the administration of these compounds. Manisfestations of the host-toxicity of the fluoropyrimidines include mainly gastrointestinal epithelial ulceration, myelosuppression and, to a lesser extent, cardiotoxicities, hepato-toxicities and neurotoxicities.

5-fluorouracil and 5-fluoro-2'-deoxyuridine themselves are inactive and must first be converted to one of their active nucleotides, 5-fluoro-2'-deoxyuridine-5'-monophosphate (FdUMP), 5-fluoro-2'-deoxyuridine-5'-triphosphate (FdUTP) or 5-fluorouridine-5-triphosphate (FUTP) before their antitumor activities can be realized. 5-fluoro-2'-deoxyuridine-5'-monophosphate inhibits the enzyme thymidylate synthase (EC 2.1.1.45) resulting in inhibition of DNA synthesis. FdUTP may be incorporated into DNA while FUTP is incorporated into various classes of RNA. These events lead to the disruption of DNA and RNA synthesis and produce the cytotoxicity of 5-fluorouracil or 5-fluoro-2'-deoxyuridine. The disruption of RNA synthesis is also believed to produce the induced host-toxicity by 5-fluorouracil.

The anabolism of 5-fluorouracil to its active 5'-monophosphate nucleotides, 5-fluorouridine-5'-monophosphate (FUMP) and 5-fluoro-2'-deoxyuridine-5'-monophosphate (FdUMP), can be carried out in a two-step process catalyzed sequentially by uridine (UrdPase, EC 2.4.2.3) and/or thymidine (dThdPase, EC 2.4.2.4) phosphorylases, followed by the action of uridine (UrdKase, E C 2.7.1.48) and/or thymidine (dThdKase, EC 2.7.1.21) kinases. Alternatively, 5-fluorouridine-5'-monophosphate can be formed in a single step by a phosphoribosyltransfer reaction catalyzed by orotate phosphoribosyltransferase (OPRTase; EC 2.4.2.10). Similarly, 5-fluoro-2'-deoxyuridine can be directly anabolized to 5-fluoro-2'-deoxyuridine-5'-monophosphate by thymidine kinase or catabolized by both uridine phosphorylase and thymidine phosphorylase to 5-fluorouracil.

It has recently been discovered that a certain population of cancer patients are intolerant to treatment with 5-fluorouracil and 5-fluoro-2'-deoxyuridine. The intolerance to 5-fluorouracil was initially attributed to a deficiency or low activity of dihydrouracil dehydrogenase (DHUDase, EC 1.3.1.2), the first enzyme in the catabolic pathway of 5-fluorouracil. However, it appeared that not all intolerant patients showed reduced dihydrouracil dehydrogenase activities. Moreover, it has also been known that cancer patients, treated with fluoropyrimidines, become resistant, i.e., develop tolerance towards these drugs.

Although, the liver is the main organ implicated in the regulation of pyrimidine metabolism, and the balance between the activity of hepatic enzymes involved in pyrimidine anabolism and catabolism determines the availability and, hence, the responses (efficacy and toxicity) to chemotherapy with fluorinated pyrimidines, assaying the levels of hepatic fluoropyrimidine metabolizing activities in patients scheduled for or undergoing treatment with the 5-fluoropyrimidines is impractical.

The prior art is deficient in the lack of an effective and simple diagnostic test for cancer patients scheduled for treatment with 5-fluorouracil or 5-fluoro-2'-deoxyuridine that predicts their tolerance or intolerance to these drugs. The present invention fulfills this longstanding need and desire in the art.

SUMMARY OF THE INVENTION

The present invention relates to novel findings that the intolerance towards the well known cancer chemotherapeutic fluoropyrimidines, 5-fluorouracil (5-FU), and its nucleoside, 5-fluoro-2'-deoxyuridine, in cancer patients is correlated with an increase in the activity of the enzyme orotate phosphoribosyltransferase (OPRTase, EC 2.4.2.10) in peripheral blood mononuclear cells (PBMC). Therefore, as is clearly demonstrated by the present invention, assaying for this activity in cancer patients can predict intolerance towards fluoropyrimidines. In addition, knowledge of the status of these activities in a patient may determine the choice of appropriate modulators, agonists or antagonists, which could amplify efficacy while minimizing host toxicity of the fluorpyrimidines.

In one embodiment of the present invention, there is provided a method of predicting whether an individual will be intolerant to the effect of fluoropyrimidines comprising the step of measuring the activity of orotate phosphoribosyltransferase in a biological sample obtained from said individual. In a most preferred embodiment of this method, orotate and 5-fluorouracil are used as the substrates.

In another embodiment of the present invention, there is provided a method of determining a non-toxic dose of 5-fluoruracil or 5-deoxyuridine in an individual in need of fluoropyrimidine therapy, comprising the step of measuring the activity of 5-fluororacil phosphoribosyltransferase (FUPRTase) with 5 -fluoruracil as a substrate in a biological sample obtained from said individual.

In yet another embodiment of the present invention, there is provided a method of preparing peripheral blood mononuclear cells for shipping and subsequent enzymatic assays.

In still yet another embodiment of the present invention, there is provided standardized enzyme assay conditions for orotate phosphoribosyltransferase and 5 -fluoruracil phosphoribosyltransferase, most preferably in peripheral blood mononuclear cells.

Other and further aspects, features, and advantages of the present invention will be apparent from the following description of the presently preferred embodiments of the invention given for the purpose of disclosure.

DETAILED DESCRIPTION OF THE INVENTION

So that the matter in which the above-recited features, advantages and objects of the invention, as well as others which will become clear, are attained and can be understood in detail, more particular descriptions of the invention briefly summarized above may be had by reference to certain embodiments thereof.

The present invention is centered on the finding that tolerance to fluoropyrimidines is accompanied by increased catabolism of the nucleoside, 5-fluorodeoxyuridine, and its base, 5-fluorouracil, resulting from the combined action of increased pyrimidine phosphorylases and dihydrouracil dehydrogenase, as well as, decreased orotate phophoribosyltransferase activities. The combined activities of these enzymes, but not 5-fluorodeoxyuridine kinase, were found to regulate the amount of fluorpyrimidines available for anabolism, which, in turn, determines both the anticancer and toxicity to the host. Thus, simultaneous routine testing of these activities would provide optimization of treatment with fluoropyrimidines, the drugs most used for anticancer treatment of solid cancers. In addition, knowledge of the status of these activities in a patient may determine the choice of appropriate modulators, agonists or antagonists, which could amplify efficacy while minimizing host toxicity of the fluorpyrimidines.

In one embodiment, the present invention may be illustrated by comparing the activity pattern of key pyrimidine-metabolizing enzymes between tolerant and intolerant patients. The present invention demonstrated that the activity of orotate phosphoribosyltransferase with 5-fluorouracil (FUPRTase) is increased in patients that are intolerant to 5-fluorouracil or 5-fluoro-2'-deoxyuridine. Therefore, determination of this enzymatic activity would serve as a diagnostic test in cancer patients scheduled for treatment with 5-fluorouracil or 5-fluoro-2'-deoxyuridine to predict their tolerance or intolerance to these drugs. Orotate phosphoribosyltransferase activity can also be used to determine the doses of the drugs to be administered as host-toxicity correlates with the level of FUPRTase. As shown below, a person having ordinary skill in this art would readily recognize whether or not fluoropyrimidines should be administered, and if so, what amounts, after performing the methods and assays illustrated by the present invention.

Human peripheral blood mononuclear cells are a convenient source of pyrimidine-metabolizing activities in patients, as they can be easily obtained since peripheral blood mononuclear cells constitute 5 to $10 \times 10^6$/ml of blood. Furthermore, in cancer patients undergoing fluoropyrimidine therapy, blood plasma pharmacokinetics indicated that the bioavailability, efficacy and host-toxicities of 5-fluorouracil and 5-fluoro-2'-deoxyuridine follow a circadian rhythm, i.e., a fixed dose may have a therapeutic or toxic effect at one time point along a 24-hr time interval, but no effect at another. See e.g., Peters et al., In Vivo 1:113–118 (1987); Petit et al., Cancer Res 48:1676–1679 (1988); and Fujii et al., Cancer Res 80:167–172 (1989). Using peripheral blood mononuclear cells as an enzyme source, it has been possible to correlate circadian bioavailability of 5-fluorouracil with a circadian pattern of DHUDase activities. Harris et al., Cancer Res 50:197–201 (1990). For these reasons, peripheral blood mononuclear cells are a good substitute for liver as an enzyme source to correlate fluoropyrimidine metabolism with pyrimidine enzymic activities. Therefore, sensitive assays to determine orotate phosphoribosyltransferase activities in human patients using 5-fluorouracil and orotate as substrates and peripheral blood mononuclear cells as an enzyme source were developed.

Thus, the present invention is directed to a method of predicting whether an individual will be intolerant to the effect of fluoropyrimidines comprising the step of measuring the amount of orotate phosphoribosyltransferase activity in a biological sample obtained from said individual. More specifically, an increased activity of orotate phosphoribosyltransferase in the biological sample indicates that the individual will be intolerant to fluoropyrimidines. A patient with a measured high level of orotate phosphoribosyltransferase activity would, therefore, not be a candidate for fluoropyrimidine treatment. In a most preferred embodiment of this method, orotate and 5-fluorouracil are used as the substrates.

Generally, the methods of the present invention may be performed on a variety of biological samples. Preferably, the biological sample is peripheral blood mononuclear cells.

A person having ordinary skill in this art would readily recognize that the activity of the enzymes of interest described herein, i.e., orotate phosphoribosyltransferase may be measured using techniques routine to persons having ordinary skill in this art. For example, orotate phosphoribosyltransferase activity may be measured isotopically or orotate phosphoribosyltransferase activity may be measured spectrophotometrically The present invention also is directed to a method of determining a non-toxic dose of 5-fluoruracil in an individual in need of fluoropyrimidine therapy, comprising the step of measuring the activity of 5-fluoruracil phosphoribosyltransferase (FUPRTase) in a biological sample obtained from said individual. In this method, detecting an increased amount of 5 -fluoruracil phosphoribosyltransferase (FUPRTase) in the biological sample, a person having ordinary skill in this art would readily recognize that the dose of 5-fluorouracil to that particular patient should be decreased.

The following examples are given for the purpose of illustrating various embodiments of the invention and are not meant to limit the present invention in any fashion.

EXAMPLE 1

Chemicals

RPMI-1640 medium, fetal calf serum (FBS) was obtained from GIBCO, Grand Island, NY; [6-$^{14}$C]orotate, [2-$^{14}$C]5-fluorouracil, [2-$^{14}$C]uridine, [2-$^{14}$C]thymidine and [2-$^{14}$C] 5-fluoro-2'-deoxyuridine, from Moravek Biochemicals, Inc., Brea, Calif.; silica gel G/UV$_{254}$ and polyethyleneimine cellulose 300 PEI/UV$_{254}$ polygram thin layer chromatography plates, from Brinkmann, Westbury, N.J.; and Bio-Rad protein assay kits from Bio-Rad Laboratories Richmond, CA. BAU (5-benzylacyclouridine) was synthesized as previously described by Niedzwicki et al., Biochem Pharmacol 31:1857–1861 (1982). All other chemicals are obtained from Sigma Chemical Co., (St. Louis, Mo.)

EXAMPLE 2

Preparation of mononuclear cells

All procedures are carried out at room temperature, using solutions preheated to 37° C. Blood samples were withdrawn in aliquots of 30 ml into 60 ml syringes, containing 5 ml heparin (1,000 Units/ml). Blood and heparin were immediately mixed by inverting the syringes. The mixture was layered onto HISTOPAQUE-1077 (15 ml), in a 50 ml conical centrifuge tube and centrifuged for 30 minutes at 400 ×g. The upper layer was then aspirated with a Pasteur pipet and discarded, while the opaque interface containing the mononuclear cells was aspirated into a fresh conical tube containing 10 ml growth medium (RPMI-1640 medium: 5% FBS:0.050M HEPES, pH 7.4) and mixed by inverting the tubes. The cells were pelleted by centrifugation for 10 minutes at 250 ×g then resuspended into fresh growth medium by gentle aspiration with a Pasteur pipet. After two more washing, the cells were suspended into 10 ml fresh growth media. Under these conditions the preparation can be maintained at room temperature for 48 hours without appreciable loss of activity.

EXAMPLE 3

Preparation of sonicates

The following buffers were used: Buffer A (20 mM potassium phosphate, pH 8.0) and Buffer B (50 mM Tris-Cl, pH 7.5). Mononuclear cells were washed 2-3 times as described above except that buffer B was substituted for the growth medium. The cells were then sonicated (1:2 v/v) in buffer B using a sonic dismembrator (Fisher model 300). The sonicate was then used as the enzyme source.

EXAMPLE 4

Enzyme assays

Enzyme activities were determined isotopically as the products, nucleotides, nucleosides, bases, β-amino-acid, etc. formed from their respective radiolabeled substrates, bases and/or nucleosides. All assays were run at 37° C. under conditions where activity was linear with time and enzyme concentration. Buffer A was used to determine UrdPase, dThdPase, FdUrdPase activities and Buffer B, UrdKase, dThdKase, FdUrdKase, orotate phosphoribosyltransferase and FUPRTase. Reactions were started by the addition of extract and stopped by boiling in a water bath for 2 minutes followed by freezing. Precipitated proteins were removed by centrifugation. A 10-25 µl aliquot of the supernatant fluid was spotted on the appropriate TLC plate and developed in the appropriate solvent system. Separated substrate and product(s) were counted on a TLC Analyzer (Berthold). The amounts of substrate and product(s) were calculated on a percentage basis.

EXAMPLE 5

Orotate phosphoribosyltransferase

Orotate phosphoribosyltransferase activity was measured isotopically by following nucleoside 5'-monophosphate and nucleoside formation from radiolabeled orotate or 5-fluorouracil. Nucleoside formation results from dephosphorylation of the nucleotide by phosphohydrolase activities. The standard assay mixture contained 20 mM phosphate buffer (pH 8.0), 1 mM DTT, 100 µM of a uridine phophorylase inhibitor, BAU (to inhibit the phosphorolysis of FUrd resulting from dephosphorylation of 5-fluorouridine-5'-monophosphate, to 5-fluorouracil), 2.5 mM 5-phophoribosylpyrophosphate (PRPP), nucleobase (3-60 µM [6-$^{14}$C]orotate or 0.12-1.2 mM [2-$^{14}$C]5-fluorouracil), and 50 µl sonicate, in a final volume of 100 µl. After termination of the reaction and centrifugation, 10 µl to 25 µl of the supernatant was spotted on PEI Cellulose TLC plates, prewashed with water. The plates were then developed with water to about 10 cm, dried, and redeveloped with 0.2 M LiCl. Orotate phosphoribosyltransferase activity was determined by measuring the sum of the products OMP, orotidine, UMP and Urd.

In the case of FUPRTase, a 10-25 µl of the supernatant was spotted on silica gel TLC plates, developed in chloroform:methanol:acetic acid (100:20:5, v/v/v), and activity determined as the sum of the products 5-fluorouridine-5'-monophosphate and 5-fluoro-2'-uridine. In the spectrophotometric assay pyrophosphatase was included in the reaction mixture. After termination of the reaction an equal volume (100 µl) of color reagent (e.g., one part $H_2SO_4$, one part 10% ascorbic acid, one part 2.5% ammonium molybdate, and two parts $H_2O$) was added to the reaction mixture and incubated at 45° C. for 30 minutes. The color density was determined spectrophotometrically. When assaying activity in patients, it is crucial that the orotate phosphoribosyltransferase assay be run with the substrate at its $K_m$ (5-fluoruracil: 482±22 µM; orotate: 7.5±3 µM) as a substrate and PRPP at 2.5 mM.

EXAMPLE 6

Pyrimidine Nucleoside Kinases

The assay mixture contained 50 mM Tris-Cl, pH 7.4; 3-60 µM radiolabeled nucleoside ([2-$^{14}$C]thymidine or [2-$^{14}$C]5-fluoro-2'-deoxyuridine); 2.5 mM ATP; 5 mM creatine phosphate; 25 mM NaF; and 50 µl of sonicate to which was added a dash of phosphocreatine kinase in a final volume of 100 µl. After termination of the reaction and centrifugation, the supernatant was spotted on silica gel TLC plates. The plates were developed in a solution of chloroform:methanol:acetic acid (56:24:4, v/v/v) to separate the nucleosides which migrate with the front from the nucleotides which remain at the origin. When assaying patients, the assays are run at about 4.4 µM 5-fluoro-2'-deoxyuridine or about 6.4 µM thymidine.

EXAMPLE 7

Pyrimidine phosphorylases

The assay mixture contained Buffer A, 33-600 µM radiolabeled nucleoside ([2-$^{14}$C]uridine, [2-$^{14}$C]thymidine or [2-$^{14}$C]5-fluoro-2'-deoxyuridine), and 50 µl of sonicate in a final volume of 100 µl. After termination of the reaction and centrifugation, the nucleosides were separated from their respective nucleobases on silica gel TLC plate developed with chloroform:methanol:acetic acid (90:5:5 v/v/v). When assaying patients, the assay is run at about 226 µM 5-fluoro-2'-deoxyuridine, about 169 µM thymidine or about 114 µM uridine.

EXAMPLE 8

Kinetic Studies and Statistical Analysis

The apparent $K_m$ and $V_{max}$, as well as the enzyme efficiency values were calculated using computer programs based on Wilkinson-Cleland procedures. Because of the number of patients used, a two-tailed t-test was applied to determine the degree of significance of the difference in enzymatic activities between healthy volunteers, tolerant and intolerant subjects. Tolerants were those subjects who could withstand an 5-fluoro-2'-deoxyuridine administered dose ranging from 19-25 mg/kg/day for various days and many cycles, whereas intolerants were those patients who could not tolerate more than 10 mg/kg/day and treatment had to be discontinued.

EXAMPLE 9

Tables I and II show the $K_m$, $V_{max}$ and the efficiency of catalysis $V_{max}/K_m$ of various pyrimidine enzymes of human liver and peripheral blood mononuclear cells, respectively. With the exception of orotate phosphoribosyltransferase, which exhibited significantly different $K_m$ values for liver and peripheral blood mononuclear cells, all other activities presented comparable $K_m$ values. These kinetic parameters were used to establish the standard assay conditions for the various fluoropyrimidines-metabolizing activities.

TABLE I

Kinetic Parameters of Enzymes of Pyrimidine Metabolism in Human Liver

| | $K_m$ | $V_{max}$ | $V_{max}/K_m$ |
|---|---|---|---|
| Phosphoribosyltransferase: | | | |
| Orotate | 4.887 ± 0.361 | 0.10 ± 0.0002 | 2.02 ± 0.16 |
| 5-Fluorouracil | 120.284 ± 10.746 | 0.0054 ± 0.0002 | 0.05 ± 0.000 |
| Nucleoside Kinases | | | |
| Uridine | 55.761 ± 4.825 | 0.031 ± 0.000 | 0.55 ± 0.05 |
| 5-Fluorouridine | 25.085 ± 5.368 | 0.013 ± 0.002 | 0.50 ± 0.12 |
| Thymidine | 6.408 ± 0.142 | 0.025 ± 0.0001 | 4.00 ± 0.09 |
| 5-Fluoro-2'-deoxy uirdine | 3.102 ± 0.124 | 0.016 ± 0.0001 | 5.17 ± 0.21 |
| Nucleoside Phosphorylase: | | | |
| Uridine | 99.103 ± 7.739 | 1.703 ± 0.040 | 172.00 ± 1.40 |
| 5-Fluorouridine | 286.48 ± 46.038 | 2.470 ± 0.175 | 8.62 ± 1.51 |
| Thymidine | 255.71 ± 24.359 | 19.471 ± 0.785 | 76.15 ± 7.88 |
| 5-Fluoro-2'-deoxy uirdine | 214.85 ± 20.973 | 24.041 ± 0.931 | 111.90 ± 11.75 |

$K_m$ is in µM; $V_{max}$ is in nmol/min/mg and $V_{max}/K_m$ is in $\text{min}^{-1} \times 10^3$

TABLE II

Kinetic Parameters of Enzymes of Pyrimidine Metabolism in Human Mononuclear Cells

| | $K_m$ | $V_{max}$ | $V_{max}/K_m$ |
|---|---|---|---|
| Phosphoribosyltransferase | | | |
| Orotate | 7.522 ± 2.961 | 0.018 ± 0.002 | 2.38 ± 0.96 |
| 5-Fluorouracil | 482.22 ± 22.091 | 0.083 ± 0.002 | 0.20 ± 0.01 |
| Nucleoside Kinases | | | |
| Uridine | 40.278 ± 10.428 | 0.027 ± 0.002 | 7.00 ± 2.00 |
| 5-Fluorouridine | 6.450 ± 0.216 | 0.015 ± 0.0001 | 2.40 ± 0.08 |
| Thymidine | | | |
| 5-Fluoro-2'-deoxy uridine | 4.387 ± 0.972 | 0.013 ± 0.0008 | 2.89 ± 0.67 |
| Nucleoside Phosphorylase: | | | |
| Uridine | 113.87 ± 32.876 | 0.431 ± 0.039 | 3.79 ± 1.15 |
| Thymidine | 168.45 ± 65.197 | 1.068 ± 0.144 | 6.34 ± 2.60 |
| 5-Fluoro-2'-deoxy uridine | 225.72 ± 25.396 | 1.404 ± 0.082 | 6.22 ± 0.79 |

$K_m$ is in µM; $V_{max}$ is in nmol/min/mg and $V_{max}/K_m$ is in $\text{min}^{-1} \times 10^3$

EXAMPLE 10

The FUPRTase reaction

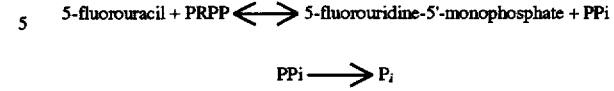

$$PPi \longrightarrow P_i$$

can be measured isotopically or spectrophotometrically using sonicates of the mononuclear cells with no appreciable background. In the spectrophotometric assay, the amount of $PP_i$ released can be determined colorimetrically by converting it to inorganic phosphate. This was achieved by including pyrophosphatase in the assay. There are, at least, two methods for determining the concentration of $P_i$ released colorimetrically, by using 1) malachite green or 2) ammonium molybdate and ascorbic acid.

In general, for obvious reasons (e.g., lack of linearity), assaying the enzymes of these pathways at the optimal substrate concentrations would not be indicative of the physiological conditions. The assay of the present invention should use 5-fluorouracil as a substrate instead of the natural substrates (e.g., orotate), since the substrate specificity of the enzyme can change due to a mutation or during or after prolonged therapy as indicated by the results herein where a difference between phosphoribosyltransferase activity using the natural substrate, orotate (orotate phosphoribosyltransferase) and 5-fluorouracil (FUPRTase) was observed.

With these considerations, the level of the different enzymes was estimated in peripheral blood mononuclear cells from normal healthy, tolerant and intolerant volunteers. TABLES III–V show that, in contrast to tolerant, intolerant patients were characterized by a significant increase in their FUPRTase activity. As mentioned above, decreased DHU-Dase activity has been associated with intolerance to 5-fluorouracil. Since the direct effect of decreased DHU-Dase activity was accumulation of 5-fluorouracil to a level compatible with the $K_m$ value of FUPRTase, it can beconcluded that the primary cause of 5-fluorouracil host-toxicities was 5-fluorouridine-5'-monophosphate formation by orotate phosphoribosyltransferase.

TABLE III

Enzyme Activities (pmol/min/mg) at $K_m$ of Means of Normal Patients

| PROBAND-TYPE | Mean-Normal | "S-D" | "n" |
|---|---|---|---|
| FdUrdPase | 3,433.0 ± | 163.4 | 9 |
| dThdPase | 2,325.0 ± | 27.4 | 6 |
| UrdPase | 606.0 ± | 27.2 | 6 |
| FdUrdKase | 25.1 ± | 3.3 | 9 |
| dThdKase | 20.0 ± | 1.8 | 9 |
| FUPRTase | 309.3 ± | 65.9 | 6 |
| OPRTase | 118.3 ± | 4.3 | 6 |

TABLE IV

Enzyme Activities (pmol/min/mg) at $K_m$ of Means of Intolerant Patients

| PROBAND-TYPE | Mean-Normal | "S-D" | "n" |
|---|---|---|---|
| FdUrdPase | 3,019.0* ± | 209.0 | 27 |
| dThdPase | 1,827.0* ± | 80.0 | 15 |
| UrdPase | 559.0 ± | 22.0 | 15 |
| FdUrdKase | 21.0 ± | 2.8 | 27 |
| dThdKase | 17.8 ± | 2.7 | 23 |

TABLE IV-continued

Enzyme Activities (pmol/min/mg) at $K_m$ of Means of Intolerant Patients

| PROBAND-TYPE | Mean-Normal | "S-D" | "n" |
|---|---|---|---|
| FUPRTase | 1,320.0[a] ± | 276.1 | 24 |
| OPRTase | 154.3[a] ± | 9.3 | 24 |

TABLE V

Enzyme Activities (pmol/min/mg) at $K_m$ of Means of Tolerant Patients

| PROBAND-TYPE | Mean-Normal | "S-D" | "n" |
|---|---|---|---|
| FdUrdPase | 3,753.0[a,b] ± | 67.8 | 12 |
| dThdPase | 2,834.0[a,b] ± | 47.3 | 6 |
| UrdPase | 497.0 ± | 56.6 | 6 |
| FdUrdKase | 22.6 ± | 2.2 | 11 |
| dThdKase | 17.6 ± | 1.9 | 9 |
| FUPRTase | 303.0[b] ± | 39.7 | 10 |
| OPRTase | 164.0[a] ± | 11.7 | 12 |

[a]Significantly different from normal volunteers at P < 0.001
[b]Significantly different from intolerant patients at P < 0.001

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of predicting whether an individual will be intolerant to the effect of fluoropyrimidines comprising the step of measuring the activity of orotate phosphoribosyltransferase activity using orotate as a substrate in a biological sample obtained from said individual, wherein an increased activity of orotate phosphoribosyltransferase in the biological sample indicates that the individual will be intolerant to fluoropyrimidines.

2. The method of claim 1, wherein said biological samples are peripheral blood mononuclear cells.

3. The method of claim 1, wherein said orotate phosphoribosyltransferase activity is measured isotopically.

4. The method of claim 1, wherein said orotate phosphoribosyltransferase activity is measured spectrophotometrically.

5. The method of claim 1, wherein the Km for orotate is from about 4.5 µM to about 10.5 µM.

6. A method of determining a non-toxic dose of 5-fluoruracil in an individual in need of fluoropyrimidine therapy, comprising the step of measuring the activity of 5-fluorouracil phosphoribosyltransferase (FUPRTase) using 5-fluorouracil as a substrate in a biological sample obtained from said individual.

7. The method of claim 6, wherein upon detecting an increased activity of 5-fluoruracil phosphoribosyltransferase (FUPRTase) in the biological sample, the dose of 5-fluorouracil is decreased.

8. The method of claim 6, wherein said biological samples are peripheral blood mononuclear cells.

9. The method of claim 6, wherein said 5-fluorouracil phosphoribosyltransferase activity is measured isotopically.

10. The method of claim 6, wherein said 5-fluorouracil phosphoribosyltransferase activity is measured spectrophotometrically.

11. The method of claim 6, wherein the Km for 5-fluorouracil is from about 460 µM to about 505 µM.

* * * * *